United States Patent
Yetkinler et al.

(10) Patent No.: US 9,707,024 B2
(45) Date of Patent: *Jul. 18, 2017

(54) USE OF VIBRATION IN COMPOSITE FIXATION

(75) Inventors: Duran N. Yetkinler, San Jose, CA (US); David Delaney, Capitola, CA (US); Brent R. Constantz, Portola Valley, CA (US)

(73) Assignee: Skeletal Kinetics, LLC, Cupertino, CA (US)

(\*) Notice: Subject to any disclaimer, the term of this patent is extended or adjusted under 35 U.S.C. 154(b) by 299 days.

This patent is subject to a terminal disclaimer.

(21) Appl. No.: 13/347,524

(22) Filed: Jan. 10, 2012

(65) Prior Publication Data

US 2012/0165822 A1 Jun. 28, 2012

Related U.S. Application Data

(63) Continuation of application No. 11/244,435, filed on Oct. 4, 2005, now Pat. No. 8,118,812, which is a continuation-in-part of application No. 10/900,019, filed on Jul. 26, 2004, now Pat. No. 7,261,718, which is a continuation-in-part of application No.

(Continued)

(51) Int. Cl.
*A61B 17/88* (2006.01)
*A61K 33/42* (2006.01)
*A61F 2/46* (2006.01)

(52) U.S. Cl.
CPC .......... *A61B 17/8822* (2013.01); *A61K 33/42* (2013.01); *A61F 2002/4683* (2013.01)

(58) Field of Classification Search
CPC ............ A61B 17/8805; A61B 17/8816; A61B 17/8819; A61B 17/8822

USPC ................................ 606/92–94; 366/123–126
See application file for complete search history.

(56) References Cited

U.S. PATENT DOCUMENTS 3,563,421 A * 2/1971 Coates .................... B06B 1/186
                                                       222/196
3,815,115 A    6/1974 Inque
3,874,372 A    4/1975 Le Bon
(Continued)

FOREIGN PATENT DOCUMENTS

DE           10057616        5/2002
EP           0353241         2/1990
(Continued)

OTHER PUBLICATIONS

Baroud et al. 'Influence of Oscillatory Mixing on the Injectability of Three Acrylic and Two Calcium-Phosphate Bone Cements for Vertebroplasty' J. Biomedical Materials Research, 2004, vol. 68B(1), pp. 105-111.

*Primary Examiner* — Anu Ramana
(74) *Attorney, Agent, or Firm* — Norton Rose Fulbright US LLP

(57) ABSTRACT

Methods of employing bone defect filling, e.g., orthopedic cements, in conjunction with hard tissue securing devices, e.g., screws, plates or rods, are provided. A feature of the subject methods is that the cement is introduced to a target bone site through a passageway of the securing device while a vibratory force is applied to the securing device. Also provided are systems and kits that find use in practicing the subject methods. The subject methods, devices and systems find use in a variety of different applications.

15 Claims, 5 Drawing Sheets

Related U.S. Application Data

10/797,907, filed on Mar. 9, 2004, now Pat. No. 7,252,672.

(56) References Cited

U.S. PATENT DOCUMENTS

| | | |
|---|---|---|
| 3,880,162 A | 4/1975 | Simmons |
| 3,980,883 A | 9/1976 | Franks |
| 4,160,012 A | 7/1979 | Ono et al. |
| 4,161,511 A | 7/1979 | Shiraki et al. |
| 4,429,691 A | 2/1984 | Niwa et al. |
| 4,463,875 A | 8/1984 | Tepic |
| 4,497,075 A | 2/1985 | Niwa et al. |
| 4,497,076 A | 2/1985 | Sullivan |
| 4,609,368 A | 9/1986 | Dotson, Jr. |
| 4,653,957 A | 3/1987 | Smith et al. |
| 4,787,751 A | 11/1988 | Bakels |
| 4,931,059 A | 6/1990 | Markham |
| 4,961,817 A | 10/1990 | Seki |
| 4,990,163 A | 2/1991 | Ducheyne et al. |
| 5,045,054 A | 9/1991 | Hood et al. |
| 5,047,030 A | 9/1991 | Draenert |
| 5,116,379 A | 5/1992 | McLardy-Smith |
| 5,167,619 A | 12/1992 | Wuchinich |
| 5,222,937 A | 6/1993 | Kagawa |
| 5,244,933 A | 9/1993 | Eidenbenz et al. |
| 5,281,265 A | 1/1994 | Liu |
| 5,304,577 A | 4/1994 | Nagata et al. |
| 5,318,570 A | 6/1994 | Hood et al. |
| 5,489,308 A | 2/1996 | Kuslich et al. |
| 5,496,399 A | 3/1996 | Ison et al. |
| 5,507,749 A | 4/1996 | Draenert |
| 5,525,148 A | 6/1996 | Chow et al. |
| 5,545,254 A | 8/1996 | Chow et al. |
| 5,554,111 A | 9/1996 | Morrey et al. |
| 5,580,623 A | 12/1996 | Fulmer et al. |
| 5,639,238 A | 6/1997 | Fishburne |
| 5,647,851 A | 7/1997 | Pokras et al. |
| 5,679,294 A | 10/1997 | Umezu et al. |
| 5,695,729 A | 12/1997 | Chow et al. |
| 5,697,981 A | 12/1997 | Ison et al. |
| 5,772,627 A | 6/1998 | Acosta et al. |
| 5,900,254 A | 5/1999 | Constantz |
| 5,954,867 A | 9/1999 | Chow et al. |
| 5,962,028 A | 10/1999 | Constantz |
| 5,968,253 A | 10/1999 | Poser et al. |
| 5,976,105 A | 11/1999 | Marcove et al. |
| 5,976,234 A | 11/1999 | Chow et al. |
| 5,997,624 A | 12/1999 | Chow et al. |
| 6,005,162 A | 12/1999 | Constantz |
| 6,027,742 A | 2/2000 | Lee et al. |
| 6,051,061 A | 4/2000 | Sawamura et al. |
| 6,083,229 A | 7/2000 | Constantz et al. |
| 6,139,320 A | 10/2000 | Hahn |
| 6,139,578 A | 10/2000 | Lee et al. |
| 6,149,655 A | 11/2000 | Constantz et al. |
| 6,214,012 B1 | 4/2001 | Karpman et al. |
| 6,224,635 B1 | 5/2001 | Ricci et al. |
| 6,241,734 B1 | 6/2001 | Scribner et al. |
| 6,273,916 B1 | 8/2001 | Murphy |
| 6,340,299 B1 | 1/2002 | Saito |
| 6,375,935 B1 | 4/2002 | Constantz |
| 6,494,611 B2 | 12/2002 | Edwards et al. |
| 6,551,337 B1 | 4/2003 | Rabiner et al. |
| 6,593,394 B1 | 7/2003 | Li et al. |
| 6,602,229 B2 | 8/2003 | Coss |
| 6,610,079 B1 | 8/2003 | Li et al. |
| 6,620,162 B2 | 9/2003 | Kuslich et al. |
| 6,638,238 B1 | 10/2003 | Weber et al. |
| 6,733,451 B2 | 5/2004 | Rabiner et al. |
| 6,808,561 B2 | 10/2004 | Genge et al. |
| 6,832,988 B2 | 12/2004 | Sproul |
| 6,872,403 B2 | 3/2005 | Pienkowski et al. |
| 2002/0155167 A1 | 10/2002 | Lee et al. |
| 2002/0183851 A1 | 12/2002 | Spiegelberg et al. |
| 2003/0199615 A1 | 10/2003 | Chaput et al. |
| 2004/0024410 A1 | 2/2004 | Olson, Jr. et al. |
| 2004/0076685 A1 | 4/2004 | Tas |

FOREIGN PATENT DOCUMENTS

| | | |
|---|---|---|
| EP | 0501595 | 9/1992 |
| EP | 1060731 A1 | 12/2000 |
| JP | 04127668 | 5/1992 |
| JP | 05317334 A | 12/1993 |
| WO | 9004953 | 5/1990 |

\* cited by examiner

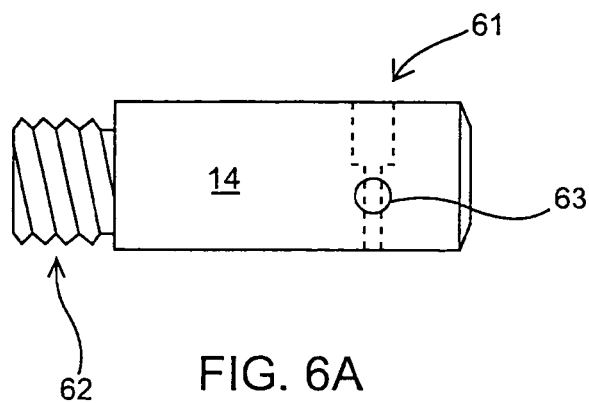
FIG. 6A
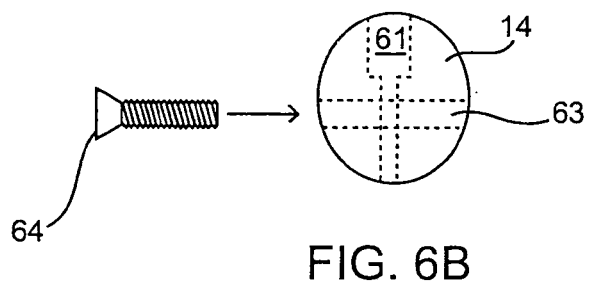
FIG. 6B
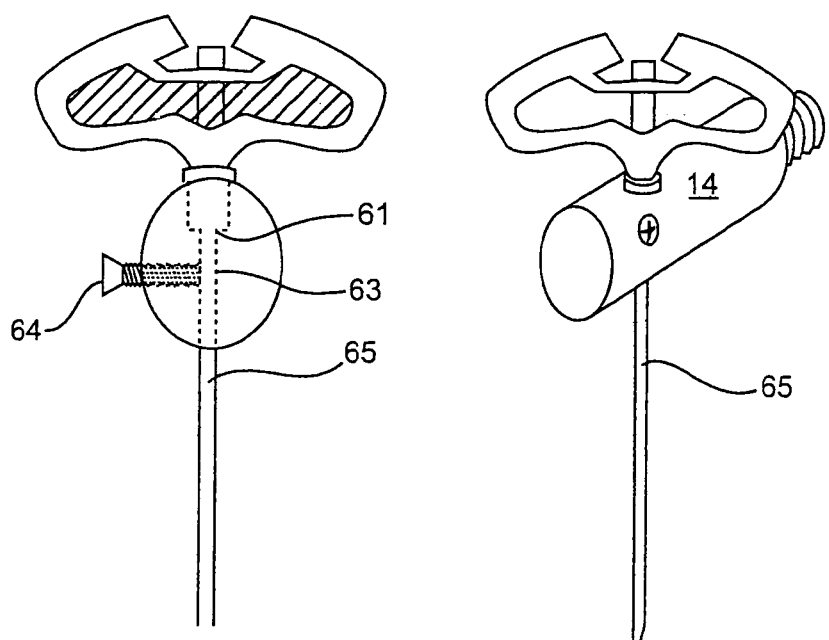
FIG. 6C
FIG. 6D

USE OF VIBRATION IN COMPOSITE FIXATION

CROSS-REFERENCE TO RELATED APPLICATIONS

This application is a continuation-in-part of application Ser. No. 10/900,019 filed on Jul. 26, 2004; which application is a continuation-in-part of application Ser. No. 10/797,907 filed on Mar. 9, 2004; the disclosures of which are herein incorporated by reference.

INTRODUCTION

Background

Orthopedic/bone defect filling cements find use in a variety of different applications, including orthopedic and dental applications. A multitude of different orthopedic cements have been developed to date, where such cements include both polymeric based cements, such as PMMA, as well as mineral based cements, e.g., calcium and/or phosphate containing cements. As the field matures, ever more chemical formulations and applications are being developed in which orthopedic cements find use.

While the field of orthopedic/bone defect filling cements has progressed greatly, there continues to be a need for improvements in this area. Where the target bone site is a porous cancellous structure, e.g., as may be encountered in a reduced fracture or inside a compromised vertebral body, one approach is to deliver the cement under high pressure, so that it adequately penetrates the cancellous bone tissue. However, a disadvantage of high-pressure delivery methods is that they can result in penetration beyond the site of interest, and delivery may be hard to control, such that even when the pressure source is removed, cement still penetrates the tissue, perhaps to undesirable areas and/or causing undesirable side effects. Specifically, pressurization of cement in the body often causes emboli of cement or fat which can result in death of the patient or other adverse events.

An alternative to delivery under pressure is to remove the cancellous tissue from the target site to produce a true void space into which the cement composition may be introduced. In certain embodiments, a void space may be produced by introducing a balloon into the target site and expanding the balloon in a manner that compresses the cancellous tissue and results in the production of a void space at the target site. However, there are disadvantages to this approach as well, such as the loss of cancellous tissue. Furthermore, the expansion of the balloon can cause fat emboli that can result in patient death or adverse events.

As such, there continues to be an interest in the development of new protocols and devices for use in applications where such cements are employed.

RELEVANT LITERATURE

United States Patents of interest include: U.S. Pat. Nos. 6,375,935; 6,139,578; 6,027,742; 6,005,162; 5,997,624; 5,976,234; 5,968,253; 5,962,028; 5,954,867; 5,900,254; 5,697,981; 5,695,729; 5,679,294; 5,580,623; 5,545,254; 5,525,148; 5,281,265; 4,990,163; 4,497,075; 4,429,691; 4,161,511 and 4,160,012. Also of interest is published United States Application No. 2004/0024410 A1. See also Baroud et al., "Influence of Oscillatory Mixing on the Injectability of Three Acrylic and Two Calcium-Phosphate Bone Cements for Vertebroplasty," J. Biomedical Materials Research, Part B-Applied Biomaterials; (Jan. 15, 2004); v. 68B, no. 1, p. 105-111.

SUMMARY OF THE INVENTION

Methods of employing bone defect filling, e.g., orthopedic cements, in conjunction with hard tissue securing devices, e.g., screws, plates or rods, to obtain composite fixation are provided. A feature of the subject methods is that the cement is introduced to a target bone site through a passageway of the securing device while a vibratory force is applied to the securing device. Also provided are systems and kits that find use in practicing the subject methods. The subject methods, devices and systems find use in a variety of different applications.

BRIEF DESCRIPTION OF THE FIGURES

FIGS. 1 to 6 provide various views of a pneumatically driven needle vibrating device that may be employed in certain embodiments of the subject invention, e.g., where vibration is indicated applied to a cannulated hard tissue securing device by applying vibration directly the delivery device while the device is jointed to the cannulation of the securing device.

DESCRIPTION OF THE SPECIFIC EMBODIMENTS

Figure 1:
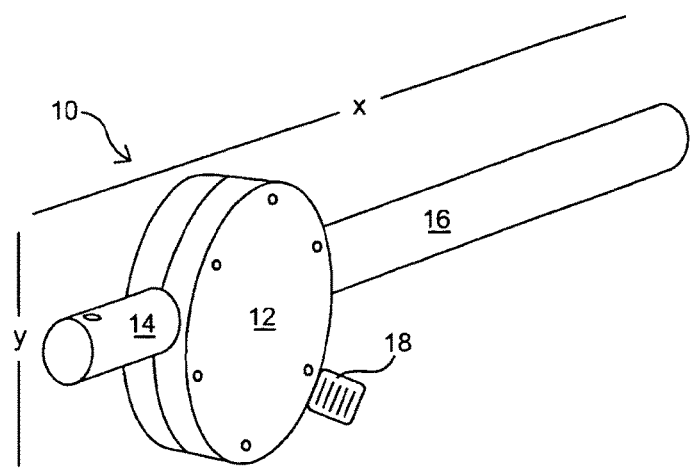

Methods of employing bone defect filling, e.g., orthopedic cements, in conjunction with hard tissue securing devices, e.g., screws, plates or rods, for composite fixation are provided. A feature of the subject methods is that the cement is introduced to a target bone site through a passageway of the securing device while a vibratory force is applied to the securing device. Also provided are systems and kits that find use in practicing the subject methods. The subject methods, devices and systems find use in a variety of different applications.

Before the present invention is described in greater detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

In further describing the subject invention, the subject methods will be described first, as well as representative utilities thereof, followed by a review of representative devices, systems and kits that may be used therein.

Methods

As summarized above, the subject methods are methods of delivering an orthopedic cement to a target bone site. A feature of the subject methods is that the cement is delivered to the target bone site through a passageway of a hard tissue securing device, e.g., a cannulation, while a vibratory force (i.e., vibration) is applied to the hard tissue securing device, either directly or indirectly. For purposes of clarity of description, representative hard tissue securing devices are reviewed first, followed by a review of representative orthopedic cements and then a more detailed discussion of the subject methods.

Hard Tissue Securing Device

The phrase "hard tissue securing device" as used herein refers to any hard tissue fixation element or structure that includes a passageway through which an orthopedic cement may be moved. In representative embodiments, hard tissue securing devices are devices that are configured to secure or fix two or more pieces of hard tissue, e.g., bone, relative to each other such that the two or more pieces do not move relative to each other. As is known in the art, such hard tissue securing or fixation devices have a variety of different configurations, where representative devices of interest include, but are not limited to: screws, rods, plates, wires, external fixation devices, e.g., pins, and the like.

A feature of the hard tissue fixation devices employed in the subject methods is that they include a passageway, as mentioned above. By "passageway" is meant a flow path (e.g., channel, duct, bore, etc.) through or along which an orthopedic cement may pass. The passageway is, in representative embodiments, bounded on all sides, such that it is configured as an elongated member having an entrance and an exit. The cross-sectional configuration of the flow path may vary significantly, and may be circular, oval, square, rectangular, or other shape, including irregular.

In representative embodiments, the internal passageway of the securing device is one that has a length which is longer that its width (e.g., internal diameter), where the length may be at least about 1.5 time longer, such as at least about 2 times longer, including at least about 3 times longer, at least about 5 times longer, at least about 10 times longer, than the width of the passageway. In representative embodiments, the width (e.g., internal diameter) of the passageway ranges from about 1 to about 20 mm, such as from about 1 to about 15 mm.

A given hard tissue securing device may include a single passageway, as described above, or a plurality of such passageways, e.g., 2 or more, 3 or more, 4 or more, etc. The passageway may be configured to have a single inlet and exit, or multiple inlets and/or exits, as desired. For example, the end of the passage through which the composition flows out during use may include multiple outlets or ports, so as to provide for even introduction of cement to the target site from the end of the passageway. In one representative embodiment, the passageway may be fenestrated with multiple outlets at one end, e.g., to provide for broad dispersion of the cement around the end of the hardware element, e.g., in the cancellous bone site. For example, a cannulated screw with a fenestrated end may be employed in certain embodiments.

As indicated above, a variety of different hard tissue securing devices may be used in the subject methods. In representative embodiments, such devices may be devices that, in the art, are conveniently referred to as cannulated devices, in that they include a passageway as described above. In many such devices, the passageway is present in order to provide for passage of the device over a guidewire during implantation, as is known in the art. This cannulation or passageway is therefore present in theses devices for another purpose, and is employed in the present invention as a delivery route for the cement to a cancellous bone target site. Representative hard tissue securing devices are now reviewed in greater detail.

In representative embodiments, the hard tissue securing device is a cannulated screw. A variety of different cannulated screws are known in the art, where such devices are generally elongated structures that include a threaded region, e.g., external threaded region and an internal bore, e.g., dimensioned for passage of a guidewire therethrough. Representative cannulated screws are disclosed in U.S. Pat. Nos. 6,635,059; 6,436,100; 6,270,501; 6,010,507; 6,004,321; 5,425,733; 5,211,647; 5,129,901 and 4,950,270; the disclosures of which with respect to cannulated screws are specifically incorporated by reference. As is known in the art, the screw may have a variety of dimensions and configurations, depending on its particular application.

Another type of cannulated hard tissue securing device of interest is a cannulated nail. Like the cannulated screw, the cannulated nail generally is an elongated structure that includes an internal bore, e.g., for passing the nail over a guidewire. Cannulated nails, including intermedullary or IM cannulated nails, are known in the art. Representative cannulated nails are disclosed in U.S. Pat. Nos. 6,783,529; 6,648,889; 6,547,791; 5,690,842; 5,645,545; 5,268,000; 4,846,162 and 4,103,683; the disclosures of which with respect to cannulated nails are specifically incorporated by reference. As is known in the art, the nail may have a variety of dimensions and configurations, depending on its particular application.

Another type of cannulated hard tissue securing device of interest is a cannulated rod. Like the cannulated nail, the cannulated rod generally is an elongated structure that includes an internal bore. Cannulated rods, including intermedullary or IM cannulated rods, are known in the art. Representative cannulated nails are disclosed in U.S. Pat. Nos. 5,562,667 and 5,643,321; the disclosures of which with respect to cannulated rods are specifically incorporated by reference. As is known in the art, the rod may have a variety of dimensions and configurations, depending on its particular application.

Yet another representative hard tissue securing device of interest is a cannulated plate. Such plates include a passageway or cannulation, e.g., for use during implantation where the plate is passed over a guidewire. A representative type of cannulated plate of interest is a cannulated blade plate, such as the cannulated blade plates sold by Synthes (Paoli, Pa.). Cannulated blade plates are also described in Grant et al., Clin. Orthop. Relat. Res. 1990 October; (259):111-3; Chin et al., Clin Orthop Relat Res. 2003 April; (409):241-9; Fuchs et al., Zentralbl Chir. 2003 January; 128 (1):22-7; and Morgan et al., Foot Ankle Int. 1999 June; 20 (6):375-8. As is known in the art, the plate may have a variety of dimensions and configurations, depending on its particular application.

Yet another representative type of hard tissue securing device of interest is an external fixation device, e.g., pins and the like, where such structures are known in the art.

The above types of cannulated hard tissue securing devices are representative of the different types of cannulated securing devices that are employed in the present invention.

Orthopedic Cements

As summarized above, a feature of the subject methods is that an orthopedic cement is delivered through the passageway of the hard tissue securing device. A wide variety of orthopedic (i.e., bone defect filling) cements may be employed according to the subject invention. Representative cements include, but are not limited to: polymeric based cements, e.g., polymethylmethacrylate (PMMA); composite cements (acrylic cements in conjunction with ceramics); and calcium and/or phosphate based cements (i.e., cements that include calcium and/or phosphate ions), e.g., calcium sulfate (sulphate) cements; magnesium amonium phosphate cements, calcium phosphate cements, cements containing radioopaque tracer particle that improve fluoroscopic visualization of the cement, etc. However, in certain embodiments of the subject methods, the orthopedic cement that is employed is one that has a specific gravity at 20° C. that is greater than about 1.0, such as greater than about 1.5, greater than about 2.0, including greater than about 2.5, e.g., greater than about 3.0 etc. In certain embodiments, the cement that is employed is one that does not require or benefit from compaction following delivery. Examples of cements that may require or benefit from compaction (and therefore are not employed in certain embodiments of the subject invention) include polymeric cements, e.g., PMMA, as well as granular type bone void filling products, such as the bone filling media described in United States Published Patent Application 2004/0024410.

Two representative types of cements that find use in the subject invention are polymeric cements and calcium phosphate cements, each of which is now described in greater detail below.

Polymeric Cements

In certain embodiments, the bone cements that are delivered according to the subject invention are polymeric materials which may include one or more different types of polymers that, in preparation, undergo a chemical reaction, e.g., a polymerization and/or cross-linking reaction, to produce a final product. The bone cements are, in representative embodiments, prepared by combining a liquid monomer and a powdered copolymer, such as methyl methacrylate and polymethyl methacrylate or methyl methacrylate styrene. As used herein, the terms "(meth)acrylate" and "poly(meth) acrylate" include the monomers and polymers, respectively, of methacrylic acid esters and acrylic acid esters, and the polymers also include the co-polymers of the compounds named.

In representative embodiments, the subject bone cement composition includes a solid finely divided powdery or granular polymer component and a liquid reactive or polymerizable, e.g., monomer, component that is also a solvent or swelling agent for the polymer component. The polymer and monomer components can be based on the acrylic, e.g., (meth)acrylate system, however, other polymeric systems can also be used. For convenience, the cement system may at times be broadly referred to as an acrylic polymer, or as based on PMMA (polymethylmethacrylate), a representative polymer component. While the invention is described herein in terms of a representative embodiment, i.e., bone cement, it is to be understood that the invention is also directed to dental/tooth cements.

More generally, the polymer component of the composition can be any methyl(meth)acrylate polymer such as methyl(meth)acrylate homopolymers and copolymers of methyl(meth)acrylate with alpha, beta-ethylenically unsaturated compounds such as vinyl acetate, alkyl (e.g., $C_2$-$C_6$) (meth)acrylates and multi-functional acrylic monomers such as alkylene dimethacrylate and alkylene diacrylates and triacrylates. These polymers generally have a molecular weight between 500,000 and 2,000,000. Methylmethacrylate homopolymers and copolymers are preferred. The reactive monomer component may be methyl acrylate or methyl methacrylate although the $C_2$-$C_4$ alkyl(meth)acrylates, such as ethyl(meth)acrylate, propyl(meth)acrylate or (n-, or iso-) butyl(meth)acrylate, can also be used.

These bone cement materials, which are themselves well known and commercially available, are usually provided with 2 parts by weight of the finely divided polymer and 1 part by weight of liquid monomer, although higher or lower ratios can also be used, and are characterized as being self-polymerizable substances which are mixed, together with a polymerization catalyst, such as dibenzoyl peroxide, and polymerization accelerator, such as dimethyl-p-toluidine, immediately prior to the operation to form a viscous liquid or pasty mass.

Curing of the bone cement composition is typically accomplished by any suitable initiator system such as from about 0.1 to about 3% by weight, such as about 0.6% of a conventional free radical initiator. The initiator can be a peroxy compound or an azo compound. For purposes of biocompatability benzoyl peroxide is a very suitable free radical initiator. The curing temperature is generally reduced to room temperature, e.g. about 25° to 30° C., by inclusion in the formulation of an activator for the peroxide catalyst which causes more rapid decomposition of the peroxide to form free radicals. Suitable peroxide catalysts include benzoyl peroxide, 2,4-dichlorobenzoyl peroxide and 4-chlorobenzoyl peroxide. Activators or accelerators for these catalysts include N,N-dialkyl anilines or N,N-dialkyl toluidines generally employed in amounts ranging from about 0.1 to 1% based on the weight of monomer present. A representative activator is N,N-di(2-hydroxyethyl)-p-toluidine. In order to provide longer shelf life for the compositions of the invention, the composition may be stored in a closed container at cold temperature. Stabilizers, such as hydroquinone or chlorophyll may also be added to the monomer compound.

Bone cements containing both activator and peroxide are provided as two-part compositions in which the activator and monomer and peroxide and polymer component may be packaged in separate containers. The proportions by weight of polymer and liquid monomer can range from about 4:1 to 1:2, preferably 3:1 to 1:1.5, such as 2:1, 1.5:1, 1:1 or 1:1.5.

Several representative cements are sold commercially and amenable for use in the subject invention. Such commercially available cements include, but are not limited to: the SIMPLEX™ bone cement (Howmedica-Stryker); the OTEOBOND™ bone cement (Zimmer); the CMW™ bone cement (Depuy); the ENDURANCE™ bone cement (Depuy); and the CORTOSS™ bone cement (Orthovita).

In certain embodiments, the cements may include imaging or "tracer" elements, e.g., radioopaque or radioopacifier elements, which provide for enhanced imaging of the cement during delivery, e.g., as visualized by radiographic imaging techniques. Representative radiopaque particles that may find use include radiopaque materials selected from a group consisting of barium sulfate, zirconium dioxide, tantalum, tungsten, platinum, gold, silver, stainless steel and titanium. Representative tracer elements and protocols for imaging the same are described in U.S. Pat. Nos. 6,309,420 and 6,273,916; the disclosures of which are herein incorporated by reference.

Calcium Phosphate Cements

In certain embodiments, the cement that is employed is a calcium phosphate cement. A variety of calcium phosphate cements may be delivered to a target site according to the subject invention. Representative cements of interest typically include dry reactants that include a calcium source and a phosphate source that are combined with a setting fluid under conditions sufficient to produce a settable, e.g., flowable or moldable, composition that sets into a calcium-phosphate containing product, sometimes even when immersed in a fluid environment.

The dry reactants may include a calcium source and a phosphate source. The dry reactants are typically particulate compositions, e.g., powders, where the particle size of the components of the particulate compositions typically ranges from about 1 to about 1000 microns, usually from about 1 to about 200 microns and more usually from about 1 to about 40 microns.

As mentioned above, the dry reactants may include a calcium source and a phosphate source. The calcium source and phosphate source may be present as a single compound or present as two or more compounds. As such, a single calcium phosphate present in the dry reactants may be the calcium source and the phosphate source. Alternatively, two or more compounds may be present in the dry reactants, where the compounds may be compounds that include calcium, phosphate or calcium and phosphate. Calcium phosphate sources of interest that may be present in the dry reactants include: MCPM (monocalcium phosphate monohydrate or $Ca(H_2PO_4)_2.H_2O$); DCPD (dicalcium phosphate dihydrate, brushite or $CaHPO_4.2H_2O$); ACP (amorphous calcium phosphate or $Ca_3(PO_4)_2H_2O$); DCP (dicalcium phosphate, monetite or $CaHPO_4$); tricalcium phosphate, including both α- and β-$(Ca_3(PO_4)_2$, tetracalcium phosphate $(Ca_4(PO_4)_2O$, etc. Calcium sources of interest include, but are not limited to: calcium carbonate ($CaCO_3$), calcium oxide (CaO), calcium hydroxide ($Ca(OH)_2$) and the like. Phosphate sources of interest include, but are not limited to: Phosphoric acid ($H_3PO_4$), all soluble phosphates; MCPM (monocalcium phosphate monohydrate or $Ca(H_2PO_4)_2.H_2O$) and sodium analogs thereof, e.g., $NaH_2PO_4$, and the like.

The ratios or relative amounts of each of the disparate calcium and/or phosphate compounds in the dry reactant mixture is one that provides for the desired calcium phosphate product upon combination with the setting fluid and subsequent setting. In many embodiments, the overall ratio (i.e., of all of the disparate calcium and/or phosphate compounds in the dry reactants) of calcium to phosphate in the dry reactants ranges from about 4:1 to 0.5:1, usually from about 2:1 to 1:1 and more usually from about 1.9:1 to 1.25:1.

The second component of the calcium phosphate cement compositions is a setting fluid. The setting fluid can be any of a variety of setting fluids known to those of skill in the art. Setting fluids include a variety of physiologically compatible fluids, including, but not limited to: water (including purified forms thereof), aqueous alkanol solutions, e.g. glycerol, where the alkanol is present in minor amounts, preferably less than about 20 volume percent; pH buffered or non-buffered solutions; solutions of an alkali metal hydroxide, acetate, phosphate or carbonate, particularly sodium, more particularly sodium phosphate or carbonate, e.g., at a concentration in the range of about 0.01 to about 2M, such as from about 0.05 to about 0.5M, and at a pH in the range of about 6 to about 11, such as from about 7 to about 9, including from about 7 to about 7.5; and the like.

Of particular interest in certain embodiments is a silicate setting fluid, i.e., a setting fluid that is a solution of a soluble silicate. By solution of a soluble silicate is meant an aqueous solution in which a silicate compound is dissolved and/or suspended. The silicate compound may be any compound that is physiologically compatible and is soluble in water. By soluble in water is meant a concentration of at least about 1%, usually at least about 2% and more usually at least about 5%, where the concentration of the silicate employed typically ranges from about 0-0.1 to 20%, usually from about 0.01-5 to 15% and more usually from about 5 to 10%. Silicate setting fluids finding use with calcium phosphate cements are further described in U.S. Pat. Nos. 6,375,935 and 6,719,933; the disclosures of which are herein incorporated by reference.

A variety of calcium phosphate cement compositions are known to those of skill in the art. Cement compositions known to those of skill in the art and of interest include, but are not limited to, those described in U.S. Pat. Nos.: 6,027,742; 6,005,162; 5,997,624; 5,976,234; 5,968,253; 5,962,028; 5,954,867; 5,900,254; 5,697,981; 5,695,729; 5,679,294; 5,580,623; 5,545,254; 5,525,148; 5,281,265; 4,990,163; 4,497,075; and 4,429,691; the disclosures of which are herein incorporated by reference.

Of particular interest in certain embodiments is the cement composition disclosed U.S. Pat. Nos. 6,375,935 and 6,719,933; the disclosures of which are herein incorporated by reference.

In preparing such cements, suitable amounts of the dry reactants and the setting fluid of the cement composition to be delivered to the target site are combined to produce a settable or flowable composition. In other words, the ratio of the dry reactants to setting fluid (i.e. the liquid to solids ratio) is selected to provide for a "settable" or "flowable" composition, where by "settable" or "flowable" composition is meant a composition that goes from a first non-solid (and also non-gaseous) state to a second, solid state after setting. In many embodiments, the liquid to solids ratio is chosen to provide for a flowable composition that has a viscosity ranging from that of milk to that of modeling clay. As such, the liquids to solids ratio employed in the subject methods typically ranges from about 0.2 to 1.0, usually from about 0.3 to 0.6. Of particular interest in many embodiments are methods that produce a paste composition, where the liquid to solids ratio employed in such methods typically ranges form about 0.25 to 0.5, usually from about 0.3 to 0.45.

The dry and liquid components are typically combined under agitation or mixing conditions, such that a homogenous composition is produced from the dry and liquid components. Mixing may be accomplished using any convenient means, including manual mixing as described in U.S. Pat. No. 6,005,162 and automated mixing as described in WO 98/28068, the disclosures of which are herein incorporated by reference. Also of interest is the device disclosed in U.S. Pat. No. 5,980,482, the disclosure of which is herein incorporated by reference.

The temperature of the environment in which combination or mixing of the dry and liquid components takes place is sufficient to provide for a product that has desired setting and strength characteristics, and typically ranges from about 0 to 50° C., usually from about 15 to 30° C. Mixing takes place for a period of time sufficient for the flowable composition to be produced, and generally takes place for a period of time ranging from about 15 to 120 seconds, usually from about 15 to 90 seconds and more usually from about 30 to 60 second.

The resultant settable compositions produced by the above-described methods are compositions that set into a biologically compatible, and often resorbable and/or remodelable, product, where the product is characterized by including calcium phosphate molecules not present in the initial reactants, i.e., that are the product of a chemical reaction among the initial reactants.

The term flowable is meant to include paste-like and even clay-like compositions, as well as more liquid compositions. As such, the viscosity time of the subject flowable compositions, defined as time periods under which the mixed composition injects through a standard Luer-lok fitting after mixing, typically ranges up to about 10 minutes; usually up to about 7 minutes, such as up to about 4 minutes. Of particular interest in many embodiments are paste compositions that have an injectable viscosity and inject in a time period ranging up to about 5 minutes, such as about up to about 4 minutes. Pastes that stay paste-like for longer periods may be displaced by bleeding bone once implanted into the body, which create a blood interface between the cement and the bone prior to the cement hardening.

The compositions produced by the subject invention set into calcium phosphate mineral containing products. By "calcium phosphate mineral containing" product is meant a solid product that includes one or more, usually primarily one, calcium phosphate mineral. In many, embodiments, the calcium phosphate mineral is one that is generally poorly crystalline, so as to be resorbable and, often, remodelable, over time when implanted into a physiologically site. The calcium to phosphate ratio in the product may vary depending on particular reactants and amounts thereof employed to produce it, but typically ranges from about 2:1 to 1.33:1, usually from about 1.8:1 to 1.4:1 and more usually from about 1:7:1 to 1.5:1. Of particular interest in many embodiments are apatitic products, which apatitic products have a calcium to phosphate ratio ranging from about 2.0:1 to 1.25:1, including both hydroxyapatite and calcium deficient analogs thereof, including carbonate substituted hydroxyapatite (i.e. dahllite), etc. The subject paste-like composition is, in many embodiments, one that is capable of setting into a hydroxyapatitic product, such as a carbonated hydroxyapatite, i.e. dahllite, having a carbonate substitution of from about 2 to about 10%, usually from about 2 to about 8% by weight of the final product.

The period of time required for the compositions to harden or "set" may vary. By set is meant: the Gilmore Needle Test (ASTM C266-89), modified with the cement submerged under 37° C. physiological saline. The set times of the subject cements may range from about 30 seconds to 30 minutes, such as from about 2 to 15 minutes and including from about 4 to 12 minutes. In representative embodiments, the flowable composition sets in a clinically relevant period of time. By clinically relevant period of time is meant that the paste-like composition sets in less than about 20 minutes, such as less than about 10 minutes and including less than about 5 minutes, where the composition remains flowable for at least about 1 minute, including at least about 2 minutes following combination or mixture of the precursor liquid and dry cement components.

The compressive strength of the product into which the settable/flowable composition sets may vary significantly depending on the particular components employed to produce it. Of particular interest in many embodiments is a product that has a compressive strength sufficient for it to serve as at least a cancellous bone structural material. By cancellous bone structural material is meant a material that can be used as a cancellous bone substitute material as it is capable of withstanding the physiological compressive loads experienced by compressive bone under at least normal physiological conditions. As such, the subject flowable paste-like material is one that sets into a product having a compressive strength of at least about 10, usually at least about 25 and more usually at least about 50 MPa, as measured by the assay described in Morgan, E F et al., 1997, Mechanical Properties of Carbonated Apatite Bone Mineral Substitute: Strength, Fracture and Fatigue Behavior. J. Materials Science: Materials in Medicine. V. 8, pp 559-570, where the compressive strength of the final apatitic product may be as high as 60 MPa or higher. Inclusion of the silicate in the setting liquid allows lower liquid to solids ratios to be employed which results in significantly higher compressive strengths. Compressive strengths can be obtained that range as high as 100 to 200 MPa. In certain embodiments, the resultant product has a tensile strength of at least about 0.5 MPa, such as at least about 1 MPa, including at least about 5 MPa, at least about 10 MPa or even 20 Mpa or more, e.g., from about 0.5 to about 10 MPa, as determined by the tensile strength assay appearing in the Experimental Section, below.

In certain embodiments, the resultant product is stable in vivo for extended periods of time, by which is meant that it does not dissolve or degrade (exclusive of the remodeling activity of osteoclasts) under in vivo conditions, e.g., when implanted into a living being, for extended periods of time. In these embodiments, the resultant product may be stable for at least about 4 months, at least about 6 months, at least about 1 year or longer, e.g., 2.5 years, 5 years, etc. In certain embodiments, the resultant product is stable in vitro when placed in an aqueous environment for extended periods of time, by which is meant that it does not dissolve or degrade in an aqueous environment, e.g., when immersed in water, for extended periods of time. In these embodiments, the resultant product may be stable for at least 2 weeks, e.g., at least about 1 month, including at least about 4 months, at least about 6 months, at least about 1 year or longer, e.g., 2.5 years, 5 years, etc. The length of the time that the implant persists is determined by the extent to which it replaced by new bone via cell-mediated remodeling, which is primarily a stress-mediated process and thus dependent on the specific anatomical site.

In many embodiments, the settable paste-like composition is capable of setting in a fluid environment, such as an in vivo environment at a bone repair site. As such, the settable paste composition can set in a wet environment, e.g., one that is filled with blood and other physiological fluids. Therefore, the site to which the flowable composition is administered during use need not be maintained in a dry state.

In certain embodiments, the cements may include imaging or "tracer" elements, e.g., radioopaque or radioopacifier elements, which provide for enhanced imaging of the cement during delivery, e.g., as visualized by radiographic imaging techniques. Representative radiopaque particles that may find use include radiopaque materials selected from a group consisting of barium sulfate, zirconium dioxide, tantalum, tungsten, platinum, gold, silver, stainless steel and titanium. Representative tracer elements and protocols for imaging the same are described in U.S. Pat. Nos. 6,309,420 and 6,273,916; the disclosures of which are herein incorporated by reference.

In certain embodiments, the cement may include a water-soluble contrast agent, as described in U.S. application Ser. No. 10/629,321; the disclosure of which is herein incorporated by reference. By water-soluble contrast agent is meant an agent that readily dissolves in water (i.e., is water-soluble), as defined above. In many embodiments, the water-soluble contrast agent is a water-soluble salt of a radio-opaque element, i.e., an element that is visible under standard imaging techniques and protocols employed by those of skill in the art, e.g., fluoroscopic X-ray imaging protocols, etc. The radio-opaque element is one that appears different from calcium when viewed using such imaging techniques, where representative elements of interest-include, but are not limited to: barium, oxalate, zirconium, tantalum, tungsten and the like. In certain embodiments, the contrast agent is a salt of an element that is incorporated into a compound of the calcium phosphate product of the flowable composition produced by the cement. For example, in certain embodiments the salt is a salt of an element that is incorporated into an apatitic compound present in the calcium phosphate product. Of particular interest are water-soluble barium salts, e.g., barium halides, including barium chloride, etc.

In certain embodiments, the cement may include an osteoclastogenic agent, as described in U.S. application Ser. No. 10/717,171; the disclosure of which is herein incorporated by reference. By osteoclastogenic agent is meant an agent that induces osteoclastogenesis, i.e., causes differentiation of hematopoietic monocyte/macrophage precursors into osteoclasts. In many embodiments, the osteoclastogenic agent is a modulator of the RANK mediated osteoclastogenesis induction pathway. As such, the agent may modulate the activity of one or more members of the RANK mediated osteoclastogenesis induction pathway, e.g., TRAF6, NK-κB1, NF-κB2, c-fos, RANKL, etc. In many embodiments, the osteoclastogenic agent is typically an enhancer of the RANK mediated osteoclastogenic induction pathway. In many embodiments, the osteoclastogenic agent is a ligand for the RANK receptor. The RANK receptor is known and described in U.S. Pat. Nos. 6,537,763; 6,528,482; 6,479,635; and 6,017,729; the disclosures of which are herein incorporated by reference.

In certain embodiments, the cement may include a barium apatite particulate composition in which the average particle size of the collection, population or set of barium apatite particles that collectively make up the contrast agent composition is selected or chosen to impart a "peppered" appearance to the cement when imaged using radiographic imaging protocols, e.g., via fluoroscopy. The average particle size of the barium apatite particulate composition ranges, in certain embodiments, from about 1 to about 1000µ, such as from about 50 to about 500µ, including from about 200 to about 400µ. The amount of particulate contrast agent that is employed in a given application may range, in certain embodiments, from about 1% to about 50%, such as from about 5% to about 50%, including from about 10% to about 35%, where in certain embodiments these percentages are percentages by weight and in other embodiments these percentages are percentages by volume. Such compositions are further described in U.S. application Ser. No. 10/851,766; the disclosure of which is herein incorporated by reference.

In certain embodiments, the cement compositions may be seeded with any of a variety of cells. A "cell", according to the present invention, is any preparation of living tissue, including primary tissue explants and preparations thereof, isolated cells, cells lines (including transformed cells), and host cells. Preferably, autologous cells are employed, but xenogeneic, allogeneic, or syngeneic cells are also useful. As such, the cells can be obtained directly from a mammalian donor, e.g., a patient's own cells, from a culture of cells from a donor, or from established cell culture lines. The mammal can be a mouse, rat, rabbit, guinea pig, hamster, cow, pig, horse, goat, sheep, cog, cat, and the mammal can be a human. Cells of the same species and preferably of the same immunological profile can be obtained by biopsy, either from the patient or a close relative. Where the cells are not autologous, it may be desirable to administer immunosuppressive agents in order to minimize rejection. In preferred embodiments, such agents may be included within the seeded composition to ensure effective local concentrations of the agents and to minimize systemic effects of their administration. The cells employed may be primary cells, explants, or cell lines, and may be dividing or non-dividing cells. Cells may be expanded ex-vivo prior to introduction into the inventive cement compositions. Autologous cells are preferably expanded in this way if a sufficient number of viable cells cannot be harvested from the host.

Any preparation of living cells may be use to seed the cement composition of the present invention. For example, cultured cells or isolated individual cells may be used. Alternatively or additionally, pieces of tissue, including tissue that has some internal structure, may be used. The cells may be primary tissue explants and preparations thereof, cell lines (including transformed cells), or host cells.

Any available methods may be employed to harvest, maintain, expand, and prepare cells for use in the present invention. Useful references that describe such procedures include, for example, Freshney, Culture of Animal Cells: a Manual of Basic Technique, Alan R. Liss Inc., New York, N.Y., incorporated herein by reference.

The cement composition material of the invention is useful as a scaffold for production of hard or soft tissues. Tissue-producing or -degrading cells that may be incorporated into the material include, but are not limited to, chondrocytes, osteocytes, osteoblasts, osteoclasts, mesenchymal stem cells, other bone- or cartilage-producing cells or cell lines, fibroblasts, muscle cells, hepatocytes, parenchymal cells, cells of intestinal origin, nerve cells, and skin cells.

Methods of isolating and culturing such tissue-producing or -degrading cells, and/or their precursors, are known in the art (see, for example, Vacanti et al., U.S. Pat. No. 5,041,138; Elgendy et al., Biomater. 14:263, 1993; Laurencin et al., J. Biomed. Res. 27:963, 1993; Freed et al., J. Cell. Biochem. 51:257, 1993; Atala et al., J. Urol. 150:745, 1993; Ishaug et al., J. Biomed. Mater. Res. 28:1445, 1994; Chu et al., J. Biomed. Mater. Res. 29:1147, 1995; Thomson et al., J. Biomater. Sci. Polymer Edn. 7:23, 1995, each of which is incorporated by reference).

For example, mesenchymal stem cells, which can differentiate into a variety of mesenchymal or connective tissues (including, for example, adipose, osseous, cartilagenous, elastic, and fibrous connective tissues), can be isolated, purified, and replicated according to known techniques (see Caplan et al., U.S. Pat. No. 5,486,359; Caplan et al., U.S. Pat. No. 5,226,914; Dennis et al., Cell Transplantation 1:23, 1992, each of which is incorporated herein by reference). Such mesenchymal cells have been studied in association with tricalcium phosphate and hydroxyapatite carriers and have been found to be capable of successful differentiation from within such carriers (see Caplan et al., U.S. Pat. No. 5,197,985, incorporated herein by reference). Similar procedures are employed to direct mesenchymal cell differentiation within the cement material of the present invention.

Of course, the present invention is not limited to the use of tissue-producing cells. Certain preferred embodiments of the invention utilize such cells, primarily because the inventive material is so well suited to tissue-regeneration applications (particularly with those involving growth of bone and/or cartilage). Any cell may be seeded into the material of the invention. In some cases, it will be desirable to include other cells in addition with tissue-producing cells.

Any convenient cell source may be employed. For example, where the material is seeded with stem cells, e.g., adult stem cells, mesenchymal stem cells, any convenient stem cell source may be employed. Stem cell sources of interest include bone marrow, cord blood, etc., which source may be treated to enrich the target stem cell population of interest, e.g., fractionated, etc.

The cells that are seeded into the cement composition may be genetically engineered, for example to produce a protein or other factor that it useful in the particular application. In preferred embodiments, cells may be engineered to produce molecules that impart resistance to host immune attack and rejection. The Fas-L and CR-1 genes are examples of useful such genes.

Generally, cells are introduced into the subject material of the present invention in vitro, although in vivo seeding approaches are employed in some circumstances. Cells are typically mixed with the cement composition prior to setting.

Any available method may be employed to introduce the cells into the cement composition material. For example, cells may be injected into the flowable cement composition (sometimes in combination with growth medium), or maybe introduced by other means such as pressure, vacuum, or osmosis. Alternatively (or additionally), cells may be layered on the flowable cement composition. In certain embodiments, it may be desirable to manually mix or knead the cells with the material paste. Cells may also be introduced into the hydrated precursor in vivo simply by placing the material in the body adjacent a source of desired cells. In some cases, it may be desirable to enhance such in vivo cell impregnation by including within the material an appropriate chemotactic factor, associative factor (i.e., a factor to which cells bind), or factor that induces differentiation of cells into the desired cell type.

As those of ordinary skill will readily appreciate, the number of cells to be introduced into the inventive material will vary based on the intended application of the seeded material and on the type of cell used. Where dividing autologous cells are being introduced by injection into the hydrated precursor, use of 20,000-1,000,000 cells per cm3 are expected to result in cellular proliferation and extracellular matrix formation within the material. Where non-dividing cells are employed, larger numbers of cells will generally be required. In those cases where seeding is accomplished by host cell migration into the material in vivo, exposure of the material to fluids containing cells (e.g., bone-forming cells), or to tissue (e.g., bone) itself has proven to be effective to seed the material with cells without the need for inoculation with a specified number of cells. The use of cells as described above is further described in U.S. Pat. No. 6,139,578 and the references cited therein, the disclosures of which are herein incorporated by reference.

Seeding a structural cement with plurlipotent cells according to the above description results in stress induced cell differentiation of the pluripotent cells, e.g., into bone forming cells, i.e., osteoblasts. As such, the subject invention provides methods of differentiating pluripotent cells into bone form cells via stress induction, wherein a sufficient amount of pluripotent cells are seeded in a structural cement as described above, which is subsequently allowed to set and, upon setting, results in stress induced differentiation of cells seeded therein as a result of mechanical forces applied to the set cement composition.

Delivery Through a Passageway of a Hard Tissue Securing Device

As summarized above, a feature of the subject methods is that the cement composition is delivered to the target bone site through the passageway of the hard tissue defect securing device while a vibratory force is applied to the securing device. In representative embodiments, a cement is employed in conjunction with securing hardware to achieve composite fixation. In composite fixation, the cement may be employed with one or more types of hardware, e.g., screws, nails, plates, wires, etc. In such embodiments, vibration may be applied to the cement via applying vibratory force to the hardware during delivery to achieve a superior composite fixation, e.g., in terms of better interface between the cement and hardware components of the composite fixation structure.

In representative embodiments, the hardware component(s) is delivered/positioned first, followed by delivery of the cement component, which cement component is delivered in conjunction with vibration according to the subject methods. The hard tissue securing device may be implanted at a target bone site using any convenient procedure developed for that device. For example, following fraction reduction, a given securing device may be implanted at the target site using known protocols for that device, where such protocols may or may include the use of manual and/or power driven tools, as is known in the art.

The term "vibratory force" is used to refer to vibration (i.e., an oscillating force) that is applied to a hard tissue securing device, where the nature of the vibratory force may vary depending on the particular embodiment of the subject invention. Any convenient representative vibratory force may be employed, where representative vibratory forces include, but are not limited to, sonic forces, mechanical forces, etc. The vibratory force may be characterized in terms of frequency, such as cycles per second (Hertz or Hz), where in certain embodiments the vibratory force applied to an object during the subject methods may have a frequency that ranges from about 0.1 to about 100,000 Hz or higher, including from about 5.0 to about 100,000 Hz or higher, e.g., from about 5.0 to about 50,000 Hz or higher, such as from about 10 to about 35,000 Hz, including from about 20 to about 20,000 Hz. In certain embodiments, the vibratory force has a frequency that is sufficient to provide for the desired outcome, e.g., full delivery of the cement without application of significant backforce (as described in greater detail below) but does not exceed about 10,000 Hz, and in certain embodiments does not exceed about 5000 Hz, and in certain embodiments does not exceed about 1000 Hz. Where the vibratory force applied to an object during the subject methods is a sonic force, the force may be infrasonic or ultrasonic, or in the audible range. The vibratory force may also be characterized in terms of its amplitude or magnitude of vibration. By "amplitude" is meant the movement in any direction. In representative embodiments, the amplitude of the applied vibratory force will range from about 1 Angstrom to about 2 mm, such as from about 1 to about 500 microns, including from about 10 to 100 microns. In certain embodiments, the amplitude of the applied vibratory force will range from about 1 Angstrom to about 1 mm, such as from about 1 to about 100 microns, including from about 10 to 50 microns. Depending on the application and desired nature of the vibratory force, the direction or orientation of the vibration may vary, where representative orientations include, but are not limited to: circular, unidirectional, random, etc. In some instance, the vibration parameters, e.g., frequency and/or amplitude, may be varied over the course or duration of the vibration usage, as may be desired depending on the particular application being performed.

The vibratory force may be applied directly or indirectly to the hard tissue securing device in a variety of different ways. For example, the force may be applied directly to the hard tissue securing device using a mechanical application element, a sonic application element, etc., as described in greater detail below. Alternatively, the force may be applied indirectly to the hard tissue securing device, e.g., the vibratory force may be applied to a delivery element that is associated with the securing device in a force transfer relationship. For example, the delivery element, e.g., cannula, syringe, etc., may be configured to mate with the entry port of the securing device passageway, and a vibratory force applied to the delivery element, where the applied vibratory force is transferred to the securing device because of the force transfer relation of the delivery element mated with the securing device.

In a representative embodiment, composite fixation according to the present invention may employ the use of what is known in the art as cannulated screws, i.e., screws with hollow centers which have entry and exit ports through which material can be introduced and removed from the hollow center of the screw, as reviewed above. In these embodiments, the screw(s) may be placed or positioned in the subject first, e.g., by delivery over a guidewire, according to methods known in the art. Following placement of the screw, the cement is delivered to the site, e.g., through the screw, in conjunction with vibration, where the vibratory force may be applied to the screw directly or indirectly, e.g., to a delivery device mated with the screw in a force transfer relationship and/or the cannulated screw, etc.

In representative embodiments, the amount of vibratory force that is applied to the cement, e.g., through application to the delivery element, is typically sufficient to provide for highly controlled penetration of the cement through cancellous bone tissue. By "highly controlled penetration" is meant penetration of the cement through cancellous bone tissue in manner that can be stopped at substantially the same time as cessation of vibration, such that when vibration stops, the cement no longer moves further into the cancellous tissue, and any movement of the cement into the cancellous tissues continues for no more than about 5 seconds, such as no more than about 1 to about 3 seconds.

A feature of certain embodiments of the subject methods is that the cement is delivered in manner that provides for highly controlled penetration without the use of significant back-pressure on the cement. As such, any pressure applied to the cement during delivery does not exceed about 100 psi, and is between about 1 and 100 psi in certain embodiments. In certain of these embodiments, a negative pressure may be present at the target delivery site, which negative pressure enhances entry of the cement composition to the target site. The negative pressure may be produced using any convenient protocol, e.g., the target site preparation protocol described above. Where a negative pressure is present at the target delivery site, the negative pressure may range from about 1 to about 1000 psi, including from about 10 to about 100 psi.

In representative embodiments, the cement is delivered such that it mixes with marrow etc., present at the target site, to provide a cell-seeded cement, as described above.

Where desired, vibration may also be employed at one or more points during a given orthopedic cement protocol. Typically, orthopedic cement protocols at least include, in addition to the delivery step: cement preparation, target site preparation, and optionally post delivery cement modification. Representative additional points at which vibration may be employed include, but are not limited to: cement preparation; target site preparation; and post delivery modification of the delivered cement. Each of these different representative times or points at which vibration may be employed is now reviewed separately in greater detail.

In certain embodiments of the subject invention, vibration is also used in conjunction with at least the preparation of an orthopedic cement. By used in conjunction with the preparation of an orthopedic cement is meant that vibration is employed at some point during the period in which the cement precursors of the cement, e.g., liquid and solid reagents or cement components, are combined to produce a flowable cement product composition. With many orthopedic cements of interest, dry and liquid precursors, e.g., a powder and setting liquid, are combined to a produce a flowable cement composition product that, over time, sets into a solid material. In certain embodiments of the subject invention, vibration is employed by applying a vibratory force, e.g., sonic or mechanical, to the precursors of the flowable composition, e.g., during mixing of the precursors. For example, in certain representative embodiments, vibration may be applied to the container or vessel in which the flowable cement composition is prepared, and thereby applied to the flowable cement composition as it is being prepared.

In certain of these representative embodiments, the vibratory force that is applied to the cement may have a frequency ranging from about 0.1 Hz to about 100,000 Hz, such as from about 5 Hz to about 50,000 Hz, including from about 100 Hz to about 5000 Hz, and an amplitude ranging from about 1 angstrom to about 5 mm, such as from about 1 micron to about 1 mm, including from about 10 micron to about 500 micron. Also of interest are the ranges provided above.

The vibratory force may be applied to the cement components for the duration of the preparatory time or for a portion thereof, e.g., while the initial components are combined, while additives are combined with the product of mixing of the initial components, etc. In certain representative embodiments, vibration is applied for a duration ranging from about 1 sec to about 10 minutes, such as from about 10 sec to about 5 minutes, including from about 15 sec to about 1 minute and in certain embodiments a duration ranging from about 1 sec to about 5 minutes, such as from about 10 sec to about 1 minute, including from about 15 sec to about 30 sec.

In certain embodiments, vibration is also employed in conjunction with at least preparation of the target bone site. In the subject methods, the target bone site may be any of a variety of different bone sites. In many embodiments, the target bone site is an interior target bone site, e.g., an interior region of a bone, as a cancellous domain bounded by cortical walls. Often, the target bone site is made up of cancellous tissue, into which it is desired to penetrate the orthopedic cement to produce a cancellous bone/cement composite structure. Representative cancellous bone target sites of interest include, but are not limited to, those found in: vertebral body sites, femur sites, proximal humerus sites, tibial plateau sites, calcaneous sites, distal radius sites, and the like.

In these embodiments, vibration may be applied to the target bone site using any convenient protocol, depending on the desired outcome of the use vibration in target bone site preparation. For example, in certain embodiments, preparation of the target bone site may include removal of marrow and/or other materials from the bone site, e.g., the methods may include a marrow or hematoma removal step, where material, e.g., marrow, hematoma, at the target site is removed, e.g., before and/or during delivery of the cement composition, so as to further enhance penetration of the cement into the target site. For example, the marrow may be removed by aspiration from the target bone site. More specifically, marrow may be aspirated from one side of the target site before or as cement is introduced into the other side. In these embodiments, a vibratory force may be applied to the target bone site to enhance the rate and/or efficiency of marrow, e.g., fatty marrow, removal.

In certain of these representative embodiments, the vibratory force that is applied to the target bone site may have a frequency ranging from about 1 Hz to about 100,000 Hz, such as from about 10 Hz to about 10,000 Hz, including from about 100 Hz to about 1000 Hz, and an amplitude ranging from about 1 Angstrom to about 5 mm, such as from about 1 micron to about 100 micron, including from about 5 micron to about 50 micron. In certain representative embodiments, vibration is applied for a duration ranging from about 0.1 sec to about 20 minutes (e.g., from about 0.1 sec to about 10 minutes), such as from about 1 sec to about 10 minutes (e.g., from about 1 sec to about 5 minutes), including from about 10 second to about 5 minutes (e.g., from about 10 seconds to about 1 minute). Also of interest are the ranges provided above.

In certain embodiments, vibration may be also employed in conjunction with post delivery cement modification, e.g., to modulate (for example enhance or impede) the rate of setting of the cement, as desired for a particular application. By selecting the appropriate type, duration and timing of vibratory force, the rate of setting of the cement can be modulated, e.g., increased or decreased, as desired. For example, in certain embodiments, following application or placement of an amount of a cement composition to a target bone site, it may be desirable to decrease or slow the rate at which the cement sets or hardens. For example, a vibratory force may be applied to the cement composition placed or positioned at the target bone site, e.g., to slow cement setting and provide longer time to is shape or model the positioned cement composition. For example, in certain embodiments, the cement composition, following placement, may initially set into a first configuration. A vibratory force may be applied to the cement in this first configuration in order to modify it to a second, more desirable configuration. In this manner, the configuration or shape of the positioned or placed cement composition may be fined tuned or tailored to achieve optimal results in a given application. In yet other embodiments, vibration may be applied to further assist the cement in penetrating into space adjacent to the direct site of introduction, e.g., through the cancellous structure of a vertebral body beyond the exact site of implantation or delivery.

In these embodiments where it is desired to slow or impede the rate of cement setting, e.g., by at least about 2-fold, such as by at least about 5-fold, including by at least about 10-fold, the vibratory force that is applied to the delivered cement composition may have a frequency ranging from about 1 to about 100,000 Hz, such as from about 10 to about 10,000 Hz, including from about 100 Hz to about 1000 Hz, and an amplitude ranging from about 1 Angstrom to about 5 mm, such as from about 1 micron to about 100 micron, including from about 5 micron to about 50 micron. In certain representative embodiments, vibration is applied for a duration ranging from about 0.1 sec to about 10 minutes, such as from about 1 sec to about 5 minutes, including from s about 10 sec to about 1 minute. Also of interest are the ranges provided above.

In yet other embodiments, a vibratory force is applied that enhances or accelerates the rate of setting of the cement, e.g., by at least about 2-fold, such as by at least about 5-fold, including by at least about 10-fold. In certain of these representative embodiments, the vibratory force that is applied to the delivered cement may have a frequency ranging from about 1 to about 100,000 Hz, such as from about 10 Hz to about 10,000 Hz, including from about 100 Hz to about 1000 Hz, and an amplitude ranging from about 1 Angstrom to about 5 mm, such as from about 1 micron to about 100 micron, including from about 5 micron to about 50 micron. In certain representative embodiments, vibration is applied for a duration ranging from about 0.1 sec to about 10 minutes, such as from about 1 sec to about 5 minute, including from about 10 sec to about 1 minute. Also of interest are the ranges provided above.

In certain embodiments, the settable cement composition is prepared at a location apart from the delivery element, e.g., syringe and needle. For example, the cement may be prepared in a mortar and pestle and then introduced into the delivery element for placement at the target site. Alternatively, the cement may be prepared in pouch or analogous structure, e.g., in its initial packaging (as described in U.S. Pat. No. 6,375,935; the disclosure of which is herein incorporated by reference). In yet other embodiments, the cement is prepared in the delivery element, e.g., syringe, as it is being vibrated according to the present invention, where the vibration of the delivery element provides the requisite agitation to combine the liquid and solid components of the cement. As such, the liquid and solid components are introduced separately into the delivery element, and vibration of the delivery element not only provides for delivery of the cement to the target site in a manner according to the invention (and described above) but also agitates or mixes the liquid and solid components to produce the flowable composition. In these latter embodiments, one may employ a delivery element that is preloaded with the liquid and solid components, where the components are separated by a frangible barrier that, upon agitation or other convenient trigger, is broken to allow mixing of the solid and liquid components, as desired.

Utility

The subject methods as described above find use in applications where it is desired to, use an orthopedic cement and an implantable securing device for composite fixation at a physiological site of interest, such as in dental, craniomaxillofacial and orthopedic applications, as well as other application in which a bone defect filling composition is employed. In orthopedic applications, the cement will generally be prepared and introduced through a passageway of a securing device that has been implanted at a bone repair site, such as a reduced fracture bone site that includes cancellous bone. The subject methods find particular use in those applications where it is desired to introduce a cement into a cancellous bone target site in a manner such that the cement penetrates the cancellous bone to produce a cancellous bone/cement composite structure, and a strong interface with the securing device employed in the composite fixation.

Representative orthopedic applications in which the invention finds particular use include the treatment of fractures and/or implant augmentation, in mammalian hosts, particularly humans. In such fracture treatment applications, the fracture may or may not be reduced first, as desired or convenient. Following any fracture reduction and implantation of the securing device, a settable structural material is introduced through the passageway of the securing device into the cancellous tissue in the fracture region using the delivery methods described above. Specific dental, craniomaxillofacial and orthopedic indications in which the subject invention finds use include, but are not limited to, those described in U.S. Pat. No. 6,149,655, the disclosure of which is herein incorporated by reference.

Systems

Also provided are systems that find use in practicing the methods of the subject invention, as described above. In representative embodiments, the subject systems at least include: a securing device, e.g., a screw, plate, nail, rod, wire, etc., a cement handling element, e.g., mixing element, delivery element, shaping element, etc.; and a vibratory element for applying a vibratory force to the delivery device, either directly or indirectly, as described above.

In certain embodiments, the delivery device and hardware are configured such that the delivery device can mate to the passageway of the hardware such that the hardware and delivery device are in a force transfer relationship. In these embodiments, the hardware and/or the delivery device may be modified to provide for the force transfer relations. For example, the systems of these embodiments may include at least: (a) a delivery device for the cement; and (b) a vibratory element for indirectly vibrating the securing device during delivery, e.g., by applying vibratory force directly to the delivery device. The delivery device in many of these representative embodiments includes a flowable composition introduction element, such as a syringe and needle, where this element is typically attached to a reservoir of the cement composition, e.g., a syringe body filled with the cement.

A feature of certain of these embodiments is that the delivery device includes an element that provides for a force transfer relationship with the hard tissue securing device, e.g., a mating interface at the end of the delivery device that mates with the entry into the passageway of the securing device. Representative mating interfaces of interest for this element include, but are not limited to: luer locks, nipple structures, nozzles, thread structures, etc., that provide for stable association of the delivery device to the hardware. For example, a cannulated screw may be threaded at one end for mating in a secure cement transfer relationship with a threaded end of a delivery element, such that the delivery element can be secured to the end of the cannulated screw.

In these representative embodiments, the vibratory element may be any convenient means for vibrating the cement composition as it is introduced by the delivery device to the target bone site. A representative type of vibratory element that may be included in the subject systems is a device that vibrates a needle or analogous structure of a cement delivery device.

A representative device that is capable of vibrating a needle to deliver a cement to a target site according to the present invention is depicted in various views in FIGS. 1 to 6. As can be seen in FIG. 1, this representative vibratory element 10 is made up of a pneumatically driven vibrating disc 12 that includes a needle holder 14. When a needle of a cement delivery device (not shown) is present in the needle holder, vibration in the disc is transferred to the needle which, in turn, is transferred to the cement composition being delivered thereby. Also shown is handle 16 (which also serves as an air intake conduit) and exhaust piece 18, through which air leaves the device. The vibratory element is dimensioned for easy use with a cement delivery element, and therefore typically ranges in length X from about 0.25 to 2.5 ft, such as from about 0.5 to about 1.5 feet, including from about 0.75 to about 1 feet; and a height Y ranging from about 0.5 to 12 in, such as from about 1 to about 10 inches, including from about 1 to about 5 inches.

Figure 2:
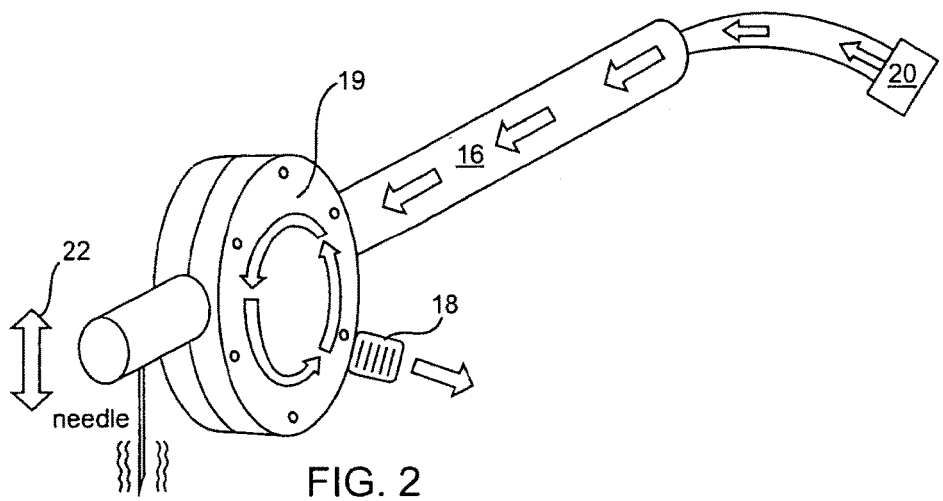

FIG. 2 provides another view of the device shown in FIG. 1, where the air flow through the device is depicted. In the device shown in FIG. 2, airflow generated by an air compressor 20 flows through the handle 16 and into an air intake port of a race or track 19 present inside of the disc. Air flows around the race and out the exhaust 18. Force produced by the air flow propels a steel bearing or ball (not shown) around the track at a high frequency. Momentum of the ball creates up and down vibration in the direction of arrow 22 that is transferred to a needle-holder and ultimately the material being dispensed by the needle. Vibration facilitates the flow of cement by reducing particle adhesion and literally "pushing" the cement downward.

Figure 3:
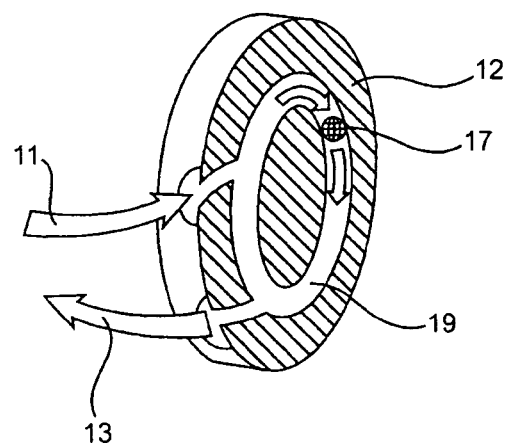

FIG. 3 provides another view of the disc 12 of the device. Shown in the depiction of FIG. 3, disc 12 includes race or track 19 around which ball 17 moves, as driven by air flowing from the intake 11 to the exhaust 13.

Figure 4:
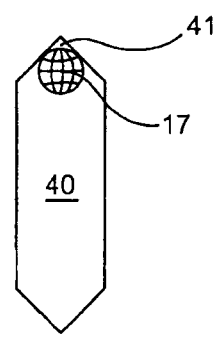

FIG. 4 provides a cross-sectional view of a representative race 40 and a ball 17 inside of the race. The race 40 has an angled end 41 along which the ball travels as it moves along the race.

Figure 5A:
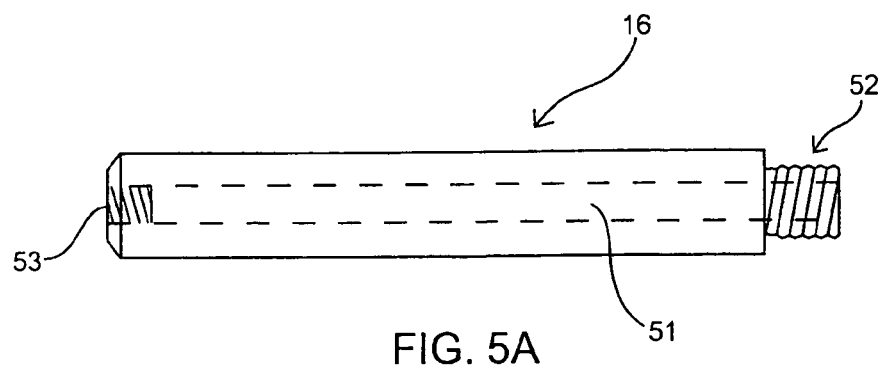
Figure 5B:
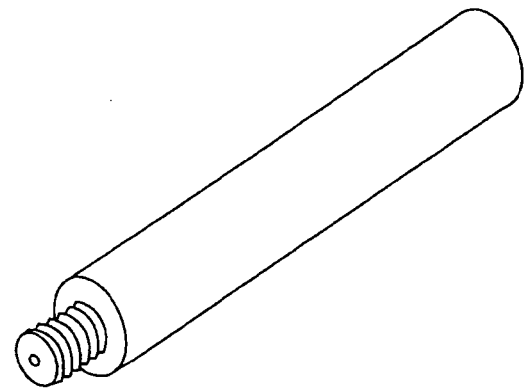

FIGS. 5A and 5B provide detailed views of the handle element 16. As shown in FIG. 5A, handle 16 includes an internal air flow passageway 51 for airflow from an external compressor to the race of the disc component 12. At one of the handle 16 is threaded disc attachment element 52, while at the other end is threaded receiving element 53 for attachment to an external air source, e.g., compressor. FIG. 5B provides an angled view of the handle shown in FIG. 5A.

FIGS. 6A to 6D provide various views of needle holder 14. FIG. 6A provides a side view of needle holder 14 showing a through-all hole 61 which is cut and countersunk to fit a delivery needle (not shown). Also shown is threaded disc attachment element 62, and through-all hole 63 for set screw. FIG. 6B provides a front view of the needle 14 showing the through-all hole 63 for the set screw 64, where hole 63 intersects hole 61. FIG. 6C shows a delivery element 65 positioned in hole 61 and held in place by set screw 64 positioned in hole 63. FIG. 6D provides an angled view of needle holder 14 holding a delivery needle 65.

Figure 7:
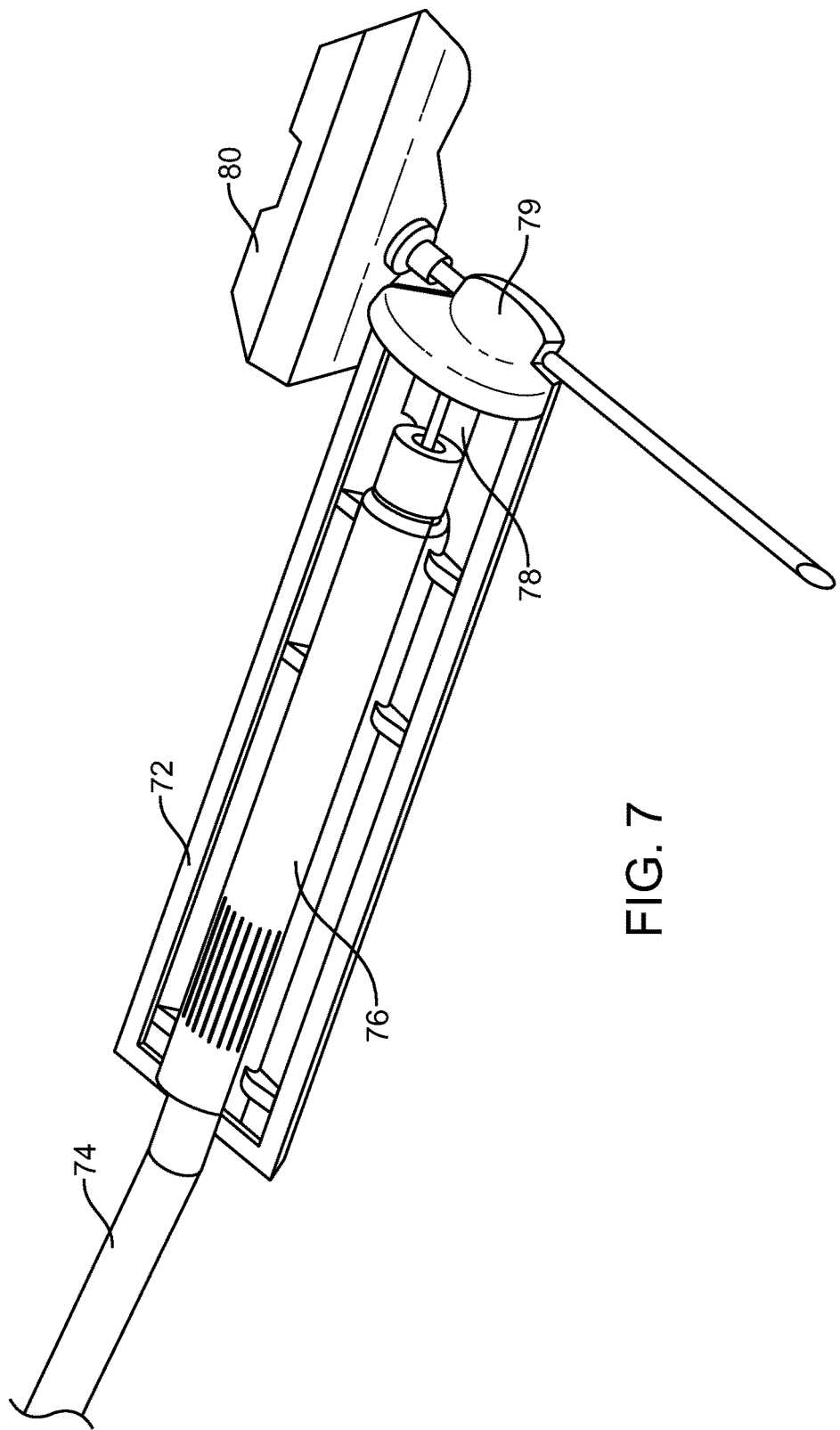
FIG. 7 provides a view of an alternatively pneumatically driven cannula vibrating device that may be employed in certain embodiments of the subject invention.

FIG. 7 provides a view of an alternative vibratory device for imparting vibration to a delivery cannula, and in doing so to a cement being delivered by the cannula. In FIG. 7, device 70 is a hand held device for imparting a vibratory force to a cement delivery cannula. Device 70 includes a housing 72 and compressed air supply 74. Compressed air supply 74 drives Variable RPM air spindle 76. Spindle 76 rotates eccentric mass 78 having a geometry selected to provide for the desired vibratory force. At the distal end of device 70 is cannula interface 79 that interfaces with and holds cannula 80 as shown.

In certain embodiments of the subject systems, the cement delivery device and the vibratory element are distinct from each other, i.e., they are separate devices. In yet other embodiments, the delivery device and vibratory element are found on a single integrated device or instrument.

In certain embodiments, the subject systems further include a cement composition or components thereof, as described above, where the components may or may not be combined into a flowable composition.

Devices

Also provided are cement delivery devices that include a vibratory element which is capable of vibrating a cement composition while it is being delivered, as described above. The vibrating element may be integral or separate from the other components of the device. For example, devices that include a vibrating cement delivery needle, where the vibration of the needle is provided by an element integral to the delivery device, are provided by the subject invention.

Kits

Also provided are kits for use in practicing the subject methods. The kits at least include one or more vibratory elements, as described above, for applying vibration to a hardware securing device, either directly or indirectly as described above. In representative embodiments, the kits also include a delivery device for delivering a cement composition, where in certain embodiments the delivery device and vibratory element may integrated into a single instrument, such that they are components of the same device.

In certain embodiments, the kits further include a calcium phosphate cement, where the dry and liquid components may be present in separate containers in the kit, or some of the components may be combined into one container, such as a kit wherein the dry components are present in a first portion and the liquid components are present in a second portion, where the portions are contained so they may or may not be present in a combined configuration, as described in U.S. Pat. No. 6,149,655, the disclosure of which is herein incorporated by reference. In certain embodiments, the kits may include two or more setting fluids in different concentrations, e.g., where one wishes to provide a kit with flexibility with respect to the nature of the setting fluid that is prepared therefrom. For example, a kit may include two more different phosphate-silicate solutions that differ from each other with respect to their silicate and/or phosphate components. Alternatively, the kit may include to or more different, separate phosphate and/or silicate solutions that differ from each other in terms is of concentration and that are mixed upon use of the kit as desired to obtain a desired setting fluid. As mentioned above, the kit components may be present in separate containers. Alternatively, the components may be present as a packaged element, such as those described above.

In certain embodiments, the kits further include a polymeric cement, where the dry and liquid components may be present in separate containers in the kit, or some of the components may be combined into one container, such as a kit wherein the dry components are present in a first portion and the liquid components are present in a second portion, where the portions are contained so they may or may not be present in a combined configuration, as described in U.S. Pat. No. 6,149,655, the disclosure of which is herein incorporated by reference. As mentioned above, the kit components may be present in separate containers. Alternatively, the components may be present as a packaged element, such as those described above.

In addition to above-mentioned components, the subject kits typically further include instructions for using the components of the kit to practice the subject methods. The instructions for practicing the subject methods are generally recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or subpackaging) etc. In other embodiments, the instructions are present as an electronic storage data file present on a suitable computer readable storage medium, e.g. CD-ROM, diskette, etc. In yet other embodiments, the actual instructions are not present in the kit, but means for obtaining the instructions from a remote source, e.g. via the internet, are provided. An example of this embodiment is a kit that includes a web address where the instructions can be viewed and/or from which the instructions can be downloaded. As with the instructions, this means for obtaining the instructions is recorded on a suitable substrate.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

What is claimed is:

1. A system for introducing an orthopedic cement to a target bone site, said system comprising:
   (a) an orthopedic calcium phosphate cement composition;
   (b) a cannulated hard tissue securing device that comprises:
      an elongated body,
      an internal passageway through which the orthopedic calcium phosphate cement composition is driven, and
      threading at an end of the elongated body; and
   (c) a cement delivery device comprising:
      (i) a needle, wherein a distal end of the needle comprises threads that mate with the threading of the cannulated hard tissue securing device such that the orthopedic calcium phosphate cement composition passes through the needle and into the internal passageway of the cannulated hard tissue securing device,
      (ii) a needle holder that secures the needle to the cement delivery device, and
      (ii) a vibratory element connected to the needle holder that vibrates the needle via a pneumatically driven vibrating disc, wherein the vibration facilitates pushing the orthopedic calcium phosphate cement composition through the needle into the internal passageway of the cannulated hard tissue securing device.

2. The system according to claim 1, wherein the cannulated hard tissue securing device is a screw.

3. The system according to claim 1, wherein the cannulated hard tissue securing device is a plate.

4. The system according to claim 1, wherein the cannulated hard tissue securing device is a nail.

5. The system according to claim 1, wherein the vibration is sufficient to provide highly controlled penetration of the cement into the target bone site without use of substantial pressure.

6. The system according to claim 1, wherein the passageway is a channel bounded on all sides, with an inlet at a first end of the cannulated hard tissue securing device and an exit at a second end of the cannulated hard tissue securing device.

7. The system according to claim 1, wherein the vibration changes a shape of the cement composition after the cement composition is received into the target bone site.

8. The system according to claim 1, wherein the vibration modulates a rate of setting of the cement composition.

9. The system according to claim 8, wherein the vibration causes the cement composition to take more time to set as compared to a length of time that the cement composition would have taken to set had the vibration not been applied.

10. The system according to claim 8, wherein the vibration causes the cement composition to take less time to set as compared to a length of time that the cement composition would have taken to set had the vibration not been applied.

11. A kit comprising:
    (a) an orthopedic calcium phosphate cement composition;
    (b) a cannulated hard tissue securing device that comprises:
       an elongated body,
       an internal passageway through which the orthopedic calcium phosphate cement composition is driven, and
       threading at an end of the elongated body; and
    (c) a cement delivery device comprising:
       (i) a needle, wherein a distal end of the needle comprises threads that mate with the threading of the cannulated hard tissue securing device such that the orthopedic calcium phosphate cement composition passes through the needle and into the internal passageway of the cannulated hard tissue securing device,
       (ii) a needle holder that secures the needle to the cement delivery device, and
       (ii) a vibratory element connected to the needle holder that vibrates the needle via a pneumatically driven vibrating disc, wherein the vibration facilitates pushing the orthopedic calcium phosphate cement composition through the needle into the internal passageway of the cannulated hard tissue securing device.

12. The kit according to claim 11, wherein the vibration changes a shape of the cement composition after the cement composition is received into a target bone site.

13. The kit according to claim 11, wherein the vibration modulates a rate of setting of the cement composition.

14. The kit according to claim 13, wherein the vibration causes the cement composition to take more time to set as compared to a length of time that the cement composition would have taken to set had the vibration not been applied.

15. The kit according to claim 14, wherein the vibration causes the cement composition to take less time to set as compared to a length of time that the cement composition would have taken to set had the vibration not been applied.

* * * * *